(12) United States Patent
Ito et al.

(10) Patent No.: US 7,718,188 B2
(45) Date of Patent: May 18, 2010

(54) TRANSDERMAL PATCH FOR EXTERNAL USE COMPRISING FENTANYL

(75) Inventors: Takeshi Ito, Tsukuba (JP); Tetsuro Tateishi, Tsukuba (JP); Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 926 days.

(21) Appl. No.: 10/531,433

(22) PCT Filed: Oct. 17, 2003

(86) PCT No.: PCT/JP03/13292

§ 371 (c)(1),
(2), (4) Date: Apr. 15, 2005

(87) PCT Pub. No.: WO2004/035054

PCT Pub. Date: Apr. 29, 2004

(65) Prior Publication Data
US 2006/0013865 A1    Jan. 19, 2006

(30) Foreign Application Priority Data
Oct. 18, 2002  (JP) .............................. 2002-304914

(51) Int. Cl.
A31F 13/00   (2006.01)
A31F 13/02   (2006.01)

(52) U.S. Cl. ....................... 424/449; 424/443; 424/447; 424/448

(58) Field of Classification Search ................. 424/448, 424/449, 447
See application file for complete search history.

(56) References Cited

U.S. PATENT DOCUMENTS

| | | | | |
|---|---|---|---|---|
| 4,588,580 A | 5/1986 | Gale et al. | .................... | 424/21 |
| 5,635,204 A | 6/1997 | Gevirtz et al. | ................ | 424/449 |
| 5,770,221 A | 6/1998 | Nakamura et al. | .......... | 424/449 |
| 5,814,032 A * | 9/1998 | Hori et al. | .................... | 604/307 |
| 5,866,157 A * | 2/1999 | Higo et al. | .................. | 424/448 |
| 6,139,866 A * | 10/2000 | Chono et al. | ................. | 424/443 |
| 2003/0109819 A1 | 6/2003 | Tsuruda et al. | ............... | 602/48 |

FOREIGN PATENT DOCUMENTS

| | | |
|---|---|---|
| JP | 61-37725 | 2/1986 |
| JP | 04-095023 | 3/1992 |
| JP | 5-507682 | 11/1993 |
| JP | 10-45570 | 2/1998 |
| JP | 2000-044476 | 2/2000 |
| WO | WO 91/16085 | 10/1991 |
| WO | WO 95/31190 | 11/1995 |
| WO | WO 01/43729 A1 | 6/2001 |
| WO | 02/074286 | 9/2002 |

OTHER PUBLICATIONS

Roy et al., "Controlled Transdermal Delivery of Fentanyl:Characterizations of Pressure-Sensitive Adhesives for Matrix Patch Design", Journal of Pharmaceutical Sciences 1996 85(5):491-495.
Office Action for corresponding Taiwan Invention Patent Application No. 92128471 dated Jun. 12, 2007.

* cited by examiner

Primary Examiner—Michael G Hartley
Assistant Examiner—Micah-Paul Young
(74) Attorney, Agent, or Firm—Licata & Tyrrell P.C.

(57) ABSTRACT

A transdermal patch for external use having a backing layer and a pressure-sensitive adhesive layer formed on one surface of the backing layer, which contains polyisobutylene, a mineral oil and fentanyl employed as the active ingredient in the pressure-sensitive adhesive layer and in which the contents of polyisobutylene and fentanyl in the pressure-sensitive adhesive layer respectively range from 75.2 to 94.2% by mass and 1 to 6% by mass while the content of the mineral oil is from 0.25 to 0.05 parts by mass based on polyisobutylene. This patch can be easily produced, has a long-lasting effect and is excellent in adhesion to the skin and tolerability against movement to the body parts.

14 Claims, 1 Drawing Sheet

* Each value stands for the mean ± S.D. of 4 Rabbits

TRANSDERMAL PATCH FOR EXTERNAL USE COMPRISING FENTANYL

This patent application is the National Stage of International Application No. PCT/JP2003/13292, filed Oct. 17, 2003, which claims the benefit of priority from Japanese Application No. 2002-304914, filed Oct. 18, 2002 each of which are herein incorporated by reference in their entirety.

DETAILED DESCRIPTION OF THE INVENTION

1. Technical Field

The invention relates to a patch which makes it possible to administer fentanyl for not less than two days and has an object of stability, skin permeability and reduction of production cost. Specifically, the invention relates to a transdermal patch for an external use, wherein it contains polyisobutylene, a mineral oil and isopropyl myristate as pressure-sensitive adhesive agents and fentanyl.

2. Background Art

As a conventional fentanyl patch, there is a fentanyl patch of reservoir-type (for example, see patent publication 1). However, the reservoir-type patch has demerits that due to enclosing a drug as a solution or semisolid into a drug reservoir, a highly precise preparation step is required not to induce the volatilization and leakage of the content, and due to necessity of a drug release controlling membrane in its structure a manufacturing process cannot avoid being complicated.

In addition, as to a fentanyl patch utilizing an ion-pair containing a drug salt and an organic acid salt, its mix pressure-sensitive adhesive base material containing SIS and PIB are disclosed respectively (for example, see patent publication 2 and patent publication 3). However, the ion-pair type patch also has demerits that due to necessity of adding a large amount of an organic acid salt to form a stable ion-pair, there are many restrictions in conditions for the manufacturing process (milling, mixing, coating, drying) while the process is complicated, and due to a high drug releasability or absorption, the progress of a drug depletion during a drug application is rapid, and it is not apt for a drug efficacy continuity of a long term exceeding one day.

Further, although a fentanyl patch of monolithic type, which contains polyisobutylene and a mineral oil as pressure-sensitive adhesive agents, is also disclosed (for example, patent publication 1), said polyisobutylene pressure-sensitive adhesive layer contains fentanyl of 10-30% in the pressure-sensitive adhesive layer, whereby in such a case there is a concern that crystallization of fentanyl in the formulation occurs as time passes by, and therefore, it is not practical from the view point of adhesion properties and a drug releasability.

On the other hand, it is known to use polyisobutylene as an adhesive. However, for example, in patent publication 4 said polyisobutylene polymer is a adhesive to percutaneously administer an active substance of oily and nonaqueous liquid, and thus it does not disclose a transdermal patch for external use comprising a solid active substance at ordinary temperature like fentanyl, which in used in the present invention, and it has a problem with regard to such as adhesiveness because it does not contain a mineral oil (for example, see Non-patent publication 1).

Patent Publication 1
JP, A, 61-37725 (page 1 to page 10)
Patent Publication 2
JP, A, 10-45570 (page 1 to page 10)
Patent Publication 3
JP, A, 2000-44476 (page 1 to page 8)
Patent Publication 4
JP, A, 5-507682 (page 1 to page 6)
Non-Patent Publication 1
Journal of Pharmaceutical Sciences, Vol. 85, No. 5, p 491, May 1996 by Samir D Roy et al.

DISCLOSURE OF THE INVENTION

Thus, an object of the invention is to provide a long-lasting transdermal patch for external use comprising fentanyl wherein the reduction of production cost is possible because the patch can easily be produced and the adhesion to the skin and tolerability against movement to the body parts of the formulation are improved comparing with those of conventional products, and further, it has high formulation stability and is excellent in the skin permeability.

As a result of extensive researches for solving the above objects, the inventors found out that by optimization of the mixing ratio of PIB, a mineral oil and fentanyl the above objects can be solved, and accomplished the invention.

Namely, the invention relates to a transdermal patch for external use having a backing layer and a pressure-sensitive adhesive layer formed on one surface of the backing layer, comprising polyisobutylene, a mineral oil and fentanyl employed as the active ingredient in the pressure-sensitive adhesive layer, the contents of polyisobutylene and fentanyl in the pressure-sensitive adhesive layer respectively ranging from 75.2 to 94.2% by mass and 1 to 6% by mass while the content of the mineral oil being from 0.25 to 0.05 parts by mass based on poyisobutylene.

In addition, the invention relates to the above patch, wherein the polyisobutylene is a mixture of a high molecular weight polyisobutylene of average molecular weight in a range from 800,000 to 1,600,000 and a low molecular weight polyisobutylene of an average molecular weight in a range from 30,000 to 80,000.

Further, the invention relates to the above patch, wherein the mass ratio between the high molecular weight polyisobutylene and the low molecular weight polyisobutylene is 1:9 to 2:3.

In addition, the invention relates to the above patch, wherein the mineral oil is liquid paraffin.

Further, the invention relates to the above patch, wherein the pressure-sensitive adhesive layer further contains a percutaneous absorption enhancer.

In addition, the invention relates to the above patch, wherein the percutaneous absorption enhancer is one or more selected from a group consisting of isopropyl myristate, isopropyl palmitate, sorbitan monooleate and oleyl alcohol.

Furthermore, the invention relates to the above patch, wherein it has an area of 5 to 80 $cm^2$ at a time of application.

As described above, the transdermal patch for external use comprising fentanyl of the invention has a pressure-sensitive adhesive agent on the backing layer, wherein the pressure-sensitive adhesive agent comprises a mixture of PIB and the mineral oil in a specified concentration, that is, 1:0.25 to 1:0.05. By such a constitution, a long-term administration of fentanyl becomes possible. Namely, according to the patch of the invention blood concentration of fentanyl can be kept not less than 1 ng/mL even at 48 to 72 hours after application. In addition, in the patch of the invention there is no cohesion failure of a pressure-sensitive adhesive agent and no remaining of an adhesive mass to the skin, and, therefore, the burden of a patient due to a long-term administration can be reduced.

Further, the transdermal patch for external use comprising fentanyl of the invention does not require a pressure-adhesive layer with a drug release controlling membrane as in a reservoir-type patch and achieves easier set up of conditions of manufacturing processes (mixing, coating, drying) compared with those of an ion-pair type patch, and, therefore, can be produced by an easier process compared with a conventional transdermal patch for external use comprising fentanyl.

MODES FOR CARRYING OUT THE INVENTION

Figure 1:
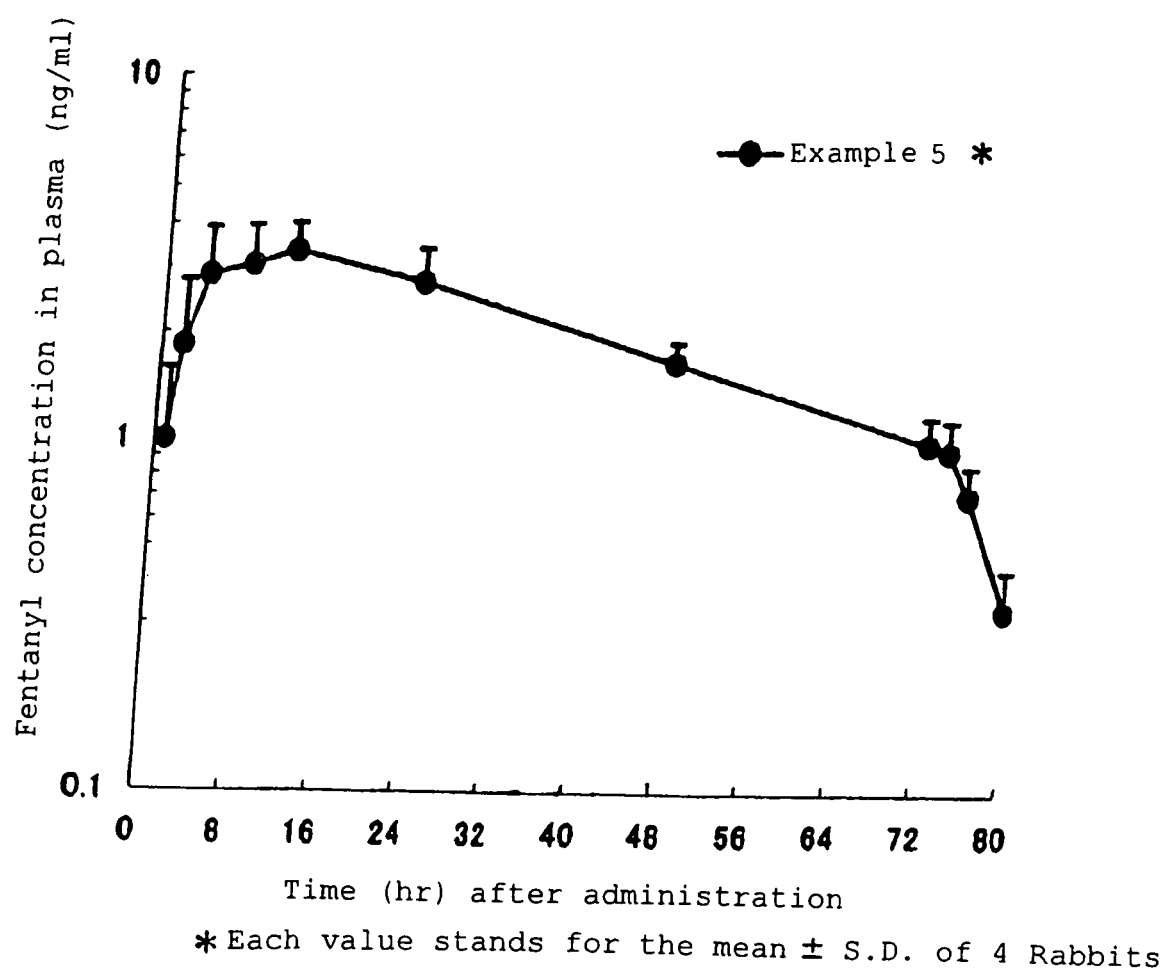
FIG. 1 shows a profile of plasma concentration of fentanyl in female rabbits after a single transdermal administration of a patch of the invention (Example 5).

In the following, the transdermal patch for external use comprising fentanyl of the invention is further explained in detail.

A pharmacologically active substance in the transdermal patch for external use comprising fentanyl of the invention is fentanyl itself and does not contain a salt thereof. Said fentanyl is contained in the pressure-sensitive adhesive layer.

Further, fentanyl is preferably in 1 to 6% based on the total mass of the pressure-sensitive adhesive layer in the patch of the invention. By the content not less than 1% by mass it becomes easy to get a sufficient amount of permeation as a transdermal patch for external use, and by making not more than 6% by mass it is possible to surely exclude bad effects due to a crystallization for physical properties of the formulation itself.

The fentanyl content of 1 to 6% by mass is preferable because a high blood concentration can be obtained. In addition, the fentanyl content from 1.5 to 2.5% by mass is particularly preferable in the aspects of physical properties of the formulation and of adhesiveness.

In addition, the pressure-sensitive adhesive agent of the patch of the invention consists of PIB, and the content of PIB may range from 75.2 to 94.2% by mass, preferably 80 to 94.2% by mass, more preferably 85 to 90% by mass. By the PIB content not less than 75.2% by mass, a sufficient adhesiveness can be obtained, and by not more than 94.2% by mass, the cohesion failure of the pressure-sensitive adhesive agent and remaining of the adhesive mass to the skin can be avoided.

When PIB contains a high molecular weight PIB and a low molecular weight PIB, a function as a pressure-sensitive adhesive agent is achieved, which is preferable in the aspect of adhesion properties.

The viscosity average molecular weight (Flory) of the high molecular weight PIB is preferably 800,000 to 1,600,000, more preferably 900,000 to 1,500,000, and particularly preferably 1,000,000 to 1,400.000.

In addition, the viscosity average molecular weight (Flory) of the low molecular weight PIB is preferably 30,000 to 80,000, more preferably 35,000 to 70,000, and particularly preferably 35,000 to 60,000.

In addition, the mass ratio between the high molecular weight polyisobutylene and the low molecular weight polyisobutylene is preferably 1:9 to 2:3, more preferably 1:7 to 1:5.

The above mixing ratio of the high molecular weight polyisobutylene and the low molecular weight polyisobutylene excludes the cohesion failure of the pressure-sensitive adhesive layer and remaining of the adhesive mass.

Meanwhile, the above average molecular weight is viscosity average molecular weight (Flory) measured by the viscosity method.

In the pressure-sensitive adhesive agent, the mineral oil is mixed in addition to PIB as described above, though the concentration ratio thereof is 1:0.25 to 1:0.05, preferably 1:0.15 to 1:0.05, more preferably 1:0.1 to 1:0.05. Mixing a mineral oil at said content enables the adhesive strength of a patch apt for a long-term administration, which is one of the objects in the invention can be obtained. As said mineral oil, there is no limitation as long as it satisfies the above object. Liquid paraffin is preferable.

Further, a percutaneous absorption enhancer for fentanyl may be contained in the pressure-sensitive adhesive agent of the patch of the invention. As to said percutaneous absorption enhancer, it may be any one or more compounds with which a percutaneous absorption enhancing effect of a drug has been known. Examples include $C_6$-$C_{20}$ fatty acids, fatty alcohols, fatty acid esters, alkyl ethers, aromatic organic acids, aromatic alcohols, aromatic fatty acid esters and aryl ethers. Furthermore, the examples include those such as lactic acid esters, acetic acid esters, monoterpene type compounds, sesquiterpene type compounds, Azone or its derivatives, glycerol fatty acid esters, sorbitan fatty acid esters, polysorbates, polyethylene glycol fatty acidesters, polyoxyethylene hardened castor oils, sucrose fatty acid esters.

Preferable examples include caprylic acid, capric acid, caproic acid, lauric acid, myristic acid, palmitic acid, stearic acid, oleic acid, linoleic acid, linolenic acid, lauryl alcohol, myristyl alcohol, oleyl alcohol, cetyl alcohol, methyl laurate, isopropyl myristate, myristyl myristate, octyl decyl myristate, cetyl palmitate, salicylic acid, methyl salicylate, glycol salicylate, cinnamic acid, methyl cinnamate, cresol, cetyl lactate, ethyl acetate, propyl acetate, isopropyl palmitate, sorbitan monooleate, geraniol, thymol, eugenol, terpineol, l-menthol, borneol, d-limonene, isoeugenol, isoborneol, nerol, dl-camphor, glycerol monolaurate, glycerol monooleate, sorbitan monolaurate, sucrose monolaurate, polysorbate 20, polyethylene glycol monolaurate, polyethylene glycol monostearate, HCO-60 (hardened caster oil), and 1-[2-(decylthio)ethyl]aza-cyclopentan-2-one (hereinafter abbreviated as pyrothiodecane), and in particular, fatty acid ester and a liphatic alcohol. In particular, isopropyl myristate, isopropyl palmitate, sorbitan monooleate and oleyl alcohol are preferred.

The above absorption enhancers may be blended in an amount of preferably 0.01 to 20% by mass, more preferably 0.1 to 10% by mass and particularly preferably 0.5 to 3% by mass based on the total mass of the pressure-sensitive adhesive layer in the formulation of the invention. The content of the absorption enhancer not more than 20% by mass prevents skin irritation such as erythema and edema, and not less than 0.01% by mass provides an effect of blending the absorption enhancer.

Further, in the patch of the invention, a hydrophilic polymer may be blended, if required, in order to absorb aqueous constituents such as sweat from the skin. Preferred hydrophilic polymers include, for example, light anhydrous silicic acid, cellulose derivatives [carboxymethyl cellulose (CMC), carboxymethyl cellulose sodium (CMCNa), methyl cellulose (MC), hydroxypropylmethyl cellulose (HPMC), hydroxypropyl cellulose (HPC), hydroxyethyl cellulose (HEC)], starch derivatives (pullulan), polyvinyl alcohol (PVA), polyvinylpyrrolidone (PVP), polyvinyl acetate (VA), carboxyvinyl polymer (CVP), ethylvinyl acetate copolymer (EVA), Eudragit, gelatin, polyacrylic acid, sodium polyacrylate, polyisobutylene-maleic anhydride copolymer, alginic acid, sodium alginate, carrageenan, Arabian gum, tragacanth gum, karaya gum and polyvinyl methacrylate. In particular, light anhydrous silicic acid, cellulose derivatives (CMCNa, HPMC, HPC, MC) and Eudragit are preferred. The hydrophilic polymer may be blended preferably in 0.01 to 20% by mass, and particularly preferably 0.5 to 10% by mass based on the total mass of the pressure-sensitive adhesive layer in the patch of the invention.

In addition, if desired, other components such as a cross-linking agent, preservative and antioxidant maybe blended in the pressure-sensitive adhesive layer in the patch of the invention. Preferable cross-linking agents include thermosetting resins such as amino resins, phenol resins, epoxy resins, alkyd resins and unsaturated polyesters, isocyanate compounds, block isocyanate compounds, organic type cross-linking agents, and inorganic type cross-linking agents such as metals or metal compounds. As the preservatives, those such as ethyl p-hydroxy benzoate, propyl p-hydroxy benzoate, butyl p-hydroxy benzoate are preferable. As the antioxidants, those such as tocopherol and its ester derivatives, ascorbic acid, ascorbic acid-stearic acid ester, nordihydroguaretic acid, dibutyl hydroxy toluene (BHT), butyl hydroxy anisole (BHA) are preferable. Further, the pressure-sensitive adhesive layer in the patch of the invention preferably consists of a nonaqueous base, higher effect of the invention being obtained with the nonaqueous base.

The pressure-sensitive adhesive layer in the patch of the invention may be manufactured by any conventional methods. For example, in case of manufacturing by a solvent method, to an organic solvent solution of a blended polymer is added the other components and stirred, and then the mixture is coated onto the backing layer and dried to obtain the formulation. Moreover, in a case that a blended polymer can be spread by a hot-melt method, the polymer ingredient is dissolved at high temperature, then added with the other ingredients, stirred, and spread on the backing layer to obtain the formulation of the invention.

In addition, in the patch of the invention, so long as the pressure-sensitive layer is constituted by the compositions as described above, and has a backing layer to support it, other layers or ingredients to constitute these are not particularly limited, whereby it may be constituted by any layers. For example, the patch of the invention may contain in addition to the backing layer and pressure-sensitive adhesive layer, those such as a release liner layer set up on the pressure-sensitive adhesive layer.

The above backing layer may comprise, for example, fabric, nonwoven fabric, polyurethane, polyester, polyvinyl acetate, polyvinylidene chloride, polyethylene, polyethylene terephthalate, paper, an aluminum sheet and the like, or composite materials thereof.

As for the patch of the invention, fentanyl is absorbed through the skin for a longer period compared with a conventional percutaneous absorption formulation. Therefore, it provides a more effective method of pain relief for patients who have difficulties with oral administration of narcotic analgesic agents. In addition, since it can be administered without invasion compared with a continues subcutaneous administration method which is an invasive administration method, it can certainly alleviate burdens of patients.

Further, the dose can easily be adjusted according to a patient's symptoms, age, body weight, sex by, for example, cutting the coated product. Although the area of the patch of the invention when applying is not particularly limited, it is preferably 5 to 80 cm$^2$, more preferably 5 to 70 cm$^2$, further preferably 5 to 45 cm$^2$. The areas of not more than 80 cm$^2$ provides favorable handling when applying, and that of not less than 5 cm$^2$ enables a sufficient blood concentration of the effective ingredient easily to be maintained.

EXAMPLE

In the following, the invention is explained in more detail by the examples. The invention, however, is not limited to these examples, and various changes may be made without departing from the spirit of the invention. Further, in the examples, '%' means '% by mass' unless otherwise specified.

Example 1

| | |
|---|---|
| High molecular PIB | 31.0% |
| Low molecular PIB | 62.0% |
| Liquid paraffin | 5.0% |
| Fentanyl | 2.0% |
| Total amount | 100.0% |

In the composition, liquid paraffin and fentanyl were stirred at room temperature, then added with toluene solution of base and stirred, and then the mixture was coated onto a PET film and dried at 110° C. for 15 min to give the pressure-sensitive adhesive layer of 50 µm, and the patch of the invention was obtained by a conventional method.

In Examples 2-6 and Comparative examples 1-3, the contents of high molecular PIB, low molecular PIB, liquid paraffin and fentanyl were changed respectively as shown below and in Table 1, and the patches were prepared in the same way as that of the example 1 except adjusting the contents of the other ingredients accordingly.

Example 2

| | |
|---|---|
| High molecular PIB | 27.0% |
| Low molecular PIB | 63.0% |
| Liquid paraffin | 9.0% |
| Fentanyl | 1.0% |
| Total amount | 100.0% |

Example 3

| | |
|---|---|
| High molecular PIB | 17.6% |
| Low molecular PIB | 70.4% |
| Liquid paraffin | 6.0% |
| Fentanyl | 6.0% |
| Total amount | 100.0% |

Example 4

| | |
|---|---|
| High molecular PIB | 36.0% |
| Low molecular PIB | 54.0% |
| Liquid paraffin | 7.0% |
| Fentanyl | 3.0% |
| Total amount | 100.0% |

Example 5

| | |
|---|---|
| High molecular PIB | 12.8% |
| Low molecular PIB | 76.7% |
| Liquid paraffin | 5.0% |
| Isopropyl myristate | 3.0% |
| Fentanyl | 2.5% |
| Total amount | 100.0% |

Example 6

| | |
|---|---|
| High molecular PIB | 63.0% |
| Low molecular PIB | 27.0% |
| Liquid paraffin | 9.0% |
| Fentanyl | 1.0% |
| Total amount | 100.0% |

Comparative Example 1

| | |
|---|---|
| High molecular PIB | 23.3% |
| Low molecular PIB | 46.7% |
| Liquid paraffin | 28.0% |
| Fentanyl | 2.0% |
| Total amount | 100.0% |

Comparative Example 2

| | |
|---|---|
| High molecular PIB | 18.6% |
| Low molecular PIB | 74.4% |
| Liquid paraffin | 1.0% |
| Fentanyl | 6.0% |
| Total amount | 100.0% |

Comparative Example 3

| | |
|---|---|
| High molecular PIB | 14.0% |
| Low molecular PIB | 56.0% |
| Liquid paraffin | 24.0% |
| Fentanyl | 6.0% |
| Total amount | 100.0% |

Test Example (Method)

Skin permeability, adhesive property, cohesive property, adhesion to the skin and remaining of adhesive mass to the skin (placebo used) of each formulation as described above were evaluated by the following methods. In addition, the overall evaluation as the formulation performance was carried out from both aspects of the skin permeability and the physical properties of the formulation based on the common standard.

(Skin Permeability Test)

Using each patch obtained in Examples 1-6 and Comparative Examples 1-3, the following tests were carried out.

First, a back part skin of a hairless mouse was extirpated, and the dermal side was placed to a receptor layer side and mounted on a flow-through cell in which warm water of 33° C. was circulated around the outer part. Then, the patch (application area of the formulation: 5 $cm^2$) was stuck on the stratum corneum side of the skin, and samplings for the receptor solutions were carried out at every one hour for 12 hours at a rate of 10 ml/hr using the saline as the receptor layer, whereby the flow amounts were measured and also the drug concentrations were measured by a high-performance liquid chromatography. The drug permeation rates per hour were calculated from the measured values to determine the drug permeation rates per unit area of the skin at a steady state. The maximum values of the drug permeation rate (maximum skin permeation rate) obtained during 12 hours from the start of the test are shown in Table 1.

(Test for Physical Properties of Formulations)

As to each formulation in the examples 1-6 and the comparative Examples 1-3, the adhesiveness was measured by a probe tack tester and a peel measuring instrument, and the cohesive properties and the adhesion to the skin were measured by a creep measuring instrument respectively. The physical properties of the formulations were evaluated by the following criteria:

◯: Good

Δ: Suitable

X. Unsuitable

In addition, the overall evaluation as the formulation performance was carried out from both aspects of the skin permeability and the physical properties of the formulation based on the same standard. The results obtained are shown in Table 1.

(Adhesion Test)

As to each formulation in the examples 1-6 and the Comparative Examples 1-3, each placebo formulation of 40 $cm^2$ was applied to the chests of 10 healthy male adult subjects for three days, and in the case that the remaining of the adhesive mass occurred when removing, the state was described.

(Pharmacokinetic Study in Rabbits)

The patch obtained in the example 5 was cut into sheets of 8 $cm^2$, and a pharmacokinetic study was carried out in the following. Namely, one sheet of the above formulation was each applied on four rabbits of Japanese White (18 week old, female, about 3 kg of body weight) whose back was shaven, and removed after 72 hours. The plasma was collected via auricle vein at 1, 2, 4, 8, 12, 24, 48, 72, 74, 76 and 80 hours after sticking of the formulation, and the fentanyl concentration in the obtained plasma was measured by LC/MS/MS. The time—fentanyl concentration in the plasma profile was shown as mean±S.D. in FIG. 1.

TABLE 1

| | Example 1 | Example 2 | Example 3 | Example 4 | Example 5 | Example 6 | Comparative example 1 | Comparative example 2 | Comparative example 3 |
|---|---|---|---|---|---|---|---|---|---|
| High molecular PIB (%) | 31.0 | 27.0 | 17.6 | 36.0 | 12.8 | 63.0 | 23.3 | 18.6 | 14.0 |
| Low molecular PIB (%) | 62.0 | 63.0 | 70.4 | 54.0 | 76.7 | 27.0 | 46.7 | 74.4 | 56.0 |
| Liquid paraffin (%) | 5.0 | 9.0 | 6.0 | 7.0 | 5.0 | 9.0 | 28.0 | 1.0 | 24.0 |
| Isopropyl myristate (%) | — | — | — | — | 3.0 | — | — | — | — |
| Fentanyl (%) | 2.0 | 1.0 | 6.0 | 3.0 | 2.5 | 1.0 | 2.0 | 6.0 | 6.0 |
| Total | 100 | 100 | 100 | 100 | 100 | 100 | 100 | 100 | 100 |
| Adhesion | ○ | ○ | ○ | ○ | ○ | Δ | ○ | X | X |
| Agglutinative property | ○ | ○ | ○ | ○ | ○ | ○ | ○ | ○ | X |
| Adhesive Property | ○ | ○ | ○ | ○ | ○ | Δ | ○ | X | ○ |
| Remaining of adhesive mass | ○ | ○ | ○ | ○ | ○ | ○ | X | ○ | X |
| Skin permeability (hairless mouse, μg/cm²/h) | 6.0 | 5.2 | 15.0 | 9.8 | 8.0 | 4.9 | 6.5 | 15.0 | 16.5 |
| Overall evaluation | ○ | ○ | ○ | ○ | ○ | Δ | X | X | X |

(Results)

As shown in Table 1, the patch of the invention was excellent in any of adhesive property, cohesive property, adhesion property and remaining of adhesive mass to the skin. On the contrary, remaining of adhesive mass to the skin occurred in Comparative Example 1 (PIB:Liquid paraffin=1:0.4) having higher liquid paraffin content than that of PIB, and adhesive property is not sufficient in Comparative Example 2 having less content (PIB:Liquid paraffin=1:0.01). When the total amount of PIB is less than 75.2% by mass, it is difficult to obtain the formulation in view of the poor physical properties.

Meanwhile, as described above, the adhesive property, cohesive property, adhesion to the skin and remaining of adhesive mass to the skin was compared among placebos, which were free from fentanyl. However, since the effect which fentanyl exerts on these physical properties is small, it is considered that the patch of the invention in which fentanyl is blended will also be excellent in the adhesive properties and the others.

In addition, the patch of the invention showed a sufficient value in the maximum skin permeation rate, which is an indicator of skin permeability (Table 1).

From the above results, it was clearly understood that the patch of the invention not only gives sufficient skin permeability of fentanyl, but also is excellent in the adhesive property, cohesive property, adhesion to the skin and remaining of adhesive mass to the skin.

With the patch of the invention, the rabbit plasma concentration of fentanyl reaches $C_{MAX}$ at about 12 hours after application, the concentration of not less than 1 ng/mL was kept till 72 hours after application. Based on this result and the general information that absorbability and the time course of plasma concentration in case of application of a fentanyl patch to the human skin is slower compared with those of rabbit (Otsuka et al, Parmacokinetics after subcutaneous or percutaneous administrations of fentanyl to rabbits, Jpn. Pharmacol. Ther. (Yakuri to Rinsyou), Vol.29, No.11, 2001, 887-897; Mizuguchi et al, Clinical evaluation of fentanyl patch (KJK-4263) toward cancer pain (1), Medicine and Drug Journal Vol. 37, No. 8, 2001/p. 2389-2402), it was clearly understood that by the patch of the invention, fentanyl blood concentration could be kept not less than 1 ng/mL during 48 to 72 hours after application to patients.

INDUSTRIAL APPLICABILITY

According to the invention, the application as a transdermal patch for external use comprising fentanyl is provided, which can easily be produced, has a long-lasting effect and is excellent in adhesion to the skin and tolerability against movement to the body parts.

The invention claimed is:

1. A transdermal patch for external use having a backing layer and a pressure-sensitive adhesive layer formed on one surface of the backing layer, said pressure-sensitive adhesive layer consisting essentially of polyisobutylene, a mineral oil and fentanyl as an active ingredient in the pressure-sensitive adhesive layer, contents of polyisobutylene and fentanyl in the pressure-sensitive adhesive layer respectively ranging from 85.0 to 93.0% by mass and 1 to 6% by mass while the content of the mineral oil being from 0.25 to 0.05 parts by mass based on polyisobutylene, wherein the pressure-sensitive adhesive layer does not contain a hydrophilic polymer.

2. A transdermal patch for external use having a backing layer and a pressure-sensitive adhesive layer formed on one surface of the backing layer, said pressure-sensitive adhesive layer consisting essentially of polyisobutylene, a mineral oil, a percutaneous absorption enhancer and fentanyl as an active ingredient in the pressure-sensitive adhesive layer, contents of polyisobutylene and fentanyl in the pressure-sensitive adhesive layer respectively ranging from 85.0 to 93.0% by mass and 1 to 6% by mass while the content of the mineral oil being from 0.25 to 0.05 parts by mass based on polyisobutylene, wherein the pressure-sensitive adhesive layer does not contain a hydrophilic polymer.

3. The patch according to claim 1, wherein the polyisobutylene is a mixture of a high molecular weight polyisobutylene of average molecular weight in a range from 800,000 to 1,600,000 and a low molecular weight polyisobutylene of average molecular weight in a range from 30,000 to 80,000.

4. The patch according to claim 3, wherein a mass ratio between the high molecular weight polyisobutylene and the low molecular weight polyisobutylene is 1:9 to 2:3.

5. The patch according to claim 1, wherein the patch has an area of 5 to 80 $cm^2$ at a time of application.

6. The patch according to claim 3, wherein the patch has an area of 5 to 80 $cm^2$ at a time of application.

7. The patch according to claim 4, wherein the patch has an area of 5 to 80 $cm^2$ at a time of application.

8. The patch according to claim 1, wherein the mineral oil is liquid paraffin.

9. The patch according to claim 2, wherein the polyisobutylene is a mixture of a high molecular weight polyisobutylene of average molecular weight in a range from 800,000 to 1,600,000 and a low molecular weight polyisobutylene of average molecular weight in a range from 30,000 to 80,000.

10. The patch according to claim 9, wherein a mass ratio between the high molecular weight polyisobutylene and the low molecular weight polyisobutylene is 1:9 to 2:3.

11. The patch according to claim 2, wherein the percutaneous absorption enhancer is one or more selected from a group consisting of isopropyl myristate, isopropyl palmitate, sorbitan monooleate and oleyl alcohol.

12. The patch according to claim 2, wherein the patch has an area of 5 to 80 $cm^2$ at a time of application.

13. The patch according to claim 11, wherein the patch has an area of 5 to 80 $cm^2$ at a time of application.

14. The patch according to claim 2, wherein the mineral oil is liquid paraffin.

* * * * *